United States Patent
Nakatou et al.

(10) Patent No.: US 10,288,580 B2
(45) Date of Patent: May 14, 2019

(54) NOX SENSOR

(71) Applicant: DENSO CORPORATION, Kariya, Aichi-pref. (JP)

(72) Inventors: Mitsunobu Nakatou, Kariya (JP); Kumi Sawaguchi, Nishio (JP); Keigo Mizutani, Nishio (JP); Takashi Araki, Kariya (JP)

(73) Assignee: DENSO CORPORATION, Kariya (JP)

(*) Notice: Subject to any disclaimer, the term of this patent is extended or adjusted under 35 U.S.C. 154(b) by 110 days.

(21) Appl. No.: 15/542,219

(22) PCT Filed: Jan. 8, 2016

(86) PCT No.: PCT/JP2016/050435
§ 371 (c)(1),
(2) Date: Jul. 7, 2017

(87) PCT Pub. No.: WO2016/111345
PCT Pub. Date: Jul. 14, 2016

(65) Prior Publication Data
US 2017/0370874 A1 Dec. 28, 2017

(30) Foreign Application Priority Data
Nov. 27, 2015 (JP) .................. 2015-232151

(51) Int. Cl.
*G01N 27/417* (2006.01)
*G01N 27/403* (2006.01)
(Continued)

(52) U.S. Cl.
CPC .......... *G01N 27/4075* (2013.01); *C22C 5/04* (2013.01); *G01N 27/12* (2013.01);
(Continued)

(58) Field of Classification Search
CPC ... G01N 27/417; G01N 27/403; G01N 27/304
See application file for complete search history.

(56) References Cited

U.S. PATENT DOCUMENTS 4,863,583 A    9/1989  Kurachi et al.
6,319,377 B1 * 11/2001  Hasei .................. G01N 27/417
                                                       204/425
(Continued)

OTHER PUBLICATIONS

U.S. Appl. No. 15/650,017 to Todo, et al., filed Jul. 14, 2017 (24 pages).

*Primary Examiner* — Susan D Leong
(74) *Attorney, Agent, or Firm* — Nixon & Vanderhye PC

(57) ABSTRACT

A NOx sensor is provided which decreases a change rate of an oxygen ion current in a sensor electrode and shortens an activation time of the sensor electrode. The NOx sensor is equipped with a solid electrolyte body, a pump electrode working to regulate an oxygen concentration in measurement gas G, and a sensor electrode working to measure the concentration of NOx in the measurement gas G. A metallic component of the sensor electrode is a Pt—Rh alloy. The mass ratio of Pt to Rh in the whole of the sensor electrode is Pt:Rh=70:30 to 35:65. The percentage of Rh in the Pt—Rh alloy in a surface layer of the sensor electrode is higher than that in the whole of the sensor electrode by an atomic composition percentage of 4 to 10 atom %.

7 Claims, 10 Drawing Sheets

(51) Int. Cl.
  *G01N 27/30* (2006.01)
  *G01N 27/407* (2006.01)
  *C22C 5/04* (2006.01)
  *G01N 27/12* (2006.01)
  *G01N 27/41* (2006.01)
  *G01N 33/00* (2006.01)

(52) U.S. Cl.
  CPC ......... *G01N 27/4076* (2013.01); *G01N 27/41* (2013.01); *G01N 33/0037* (2013.01); *Y02A 50/245* (2018.01)

(56) References Cited

U.S. PATENT DOCUMENTS

| | | |
|---|---|---|
| 2002/0005353 A1 | 1/2002 | Kato et al. |
| 2002/0162755 A1 | 11/2002 | Kato et al. |
| 2003/0201171 A1 | 10/2003 | Nakagaki et al. |
| 2004/0000479 A1* | 1/2004 | Katafuchi ............ G01N 27/419 204/424 |
| 2010/0243447 A1 | 9/2010 | Fujisaki et al. |

* cited by examiner

NOX SENSOR

This application is the U.S. national phase of International Application No. PCT/JP2016/050435 filed Jan. 8, 2016 which designated the U.S. and claims priority to JP Patent Application No. 2015-002387 filed Jan. 8, 2015 and JP Patent Application No. 2015-232151 filed Nov. 27, 2015, the entire contents of each of which are hereby incorporated by reference.

TECHNICAL FIELD

The present invention generally relates to a NOx sensor which works to measure the concentration of NOx (nitrogen oxide) in an oxygen-containing gas.

BACKGROUND ART

Typical gas sensors designed to measure the concentration of NOx are equipped with an electrode (which will be referred to below as a pump electrode) which works to regulate the oxygen concentration of oxygen-containing measurement gas (exhaust gas) and an electrode (which will be referred to below as a sensor electrode) which works to measure the concentration of NOx in the measurement gas whose oxygen concentration has been regulated. The pump electrode contains Pt (platinum) as a metallic component. The sensor electrode contains Rh (rhodium) as a metallic component in addition to Pt.

For instance, Japanese Patent No. 3701114 teaches a method of avoiding oxidization of a NOx decomposing electrode. The method uses a cermet electrode as the NOx decomposing electrode made of a Pt—Rh alloy and a ceramic component. The cermet electrode has a ratio of Pt to Rh which is selected to be Pt:Rh=10:90 to 50:50 in terms of a weight ratio. Such a ratio of Pt to Rh in the NOx decomposing electrode is described as reducing the oxidization and re-metallization of Rh. Japanese Patent First Publication No. 2003-322634 discloses a NOx decomposing electrode and a NOx concentration measuring device and teaches a weight ratio of Pt to Rh in a cermet electrode layer which is selected to be Pt:Rh=10:90 to 90:10.

SUMMARY OF THE INVENTION

Problem to be Solved by the Invention

The above gas sensors are engineered to apply voltage between the sensor electrode and a reference electrode which faces the sensor electrode through a solid electrolyte body for creating limiting current characteristics. The limiting current characteristics are characteristics in which an oxygen ion current flowing between the sensor electrode and the reference electrode is maintained nearly constant regardless of a change in the voltage. As indexes representing the performance of the sensor electrode, there are a change rate of the oxygen ion current in the sensor electrode which is associated with the ability to decompose NOx and an activation time required by the sensor electrode to become operational after the gas sensor is activated.

In the above two patent publications, the ratio of Pt to Rh in the Pt—Rh alloy is kept constant entirely over the electrodes. The publications are also silent about measures to decrease the change rate of the oxygen ion current in the sensor electrode and shorten the activation time required by the sensor electrode.

The invention was made in view of the above background. It is an object to provide a NOx sensor which is designed to minimize a change rate of an oxygen ion current in a sensor electrode and shorten an activation time of the sensor electrode.

Means for Solving the Problem

One aspect of the invention is a NOx sensor (1) which comprises:

one or a plurality of solid electrolyte bodies (2) which have oxygen ion conductivity;

a pump electrode (21) which is disposed on a surface (201) of the solid electrolyte body which is exposed to measurement gas (G) containing oxygen, the pump electrode being used to regulate an oxygen concentration in said measurement gas; and a sensor electrode (22) which is disposed on the surface of the solid electrolyte body which is exposed to the measurement gas and is used to measure a concentration of NOx in the measurement gas whose oxygen concentration has been regulated.

A metallic component of the sensor electrode is a Pt—Rh alloy.

A mass ratio of Pt to Rh in a whole of the sensor electrode is Pt:Rh=70:30 to 35:65.

A percentage of Rh in the Pt—Rh alloy in a surface layer (221) ranging from an outer surface (220) of the sensor electrode to a depth of 350 nm is higher than a percentage of Rh in the Pt—Rh alloy in a whole of the sensor electrode by an atomic composition percentage of 4 to 10 atom %.

Effect of the Invention

The NOx sensor 1 defines compositions of the surface layer of the sensor electrode (i.e., a layer from the surface to a depth of 350 nm) used in measuring the concentration of NOx in the measurement gas.

Specifically, a mass ratio of Pt (platinum) to Rh (Rhodium) in the whole of the sensor electrode is Pt:Rh=70:30 to 35:65. The mass ratio is expressed in terms of an atomic composition percentage. A Pt content of the sensor electrode relative to the whole of the Pt—Rh alloy of the sensor electrode is 22.1 to 55.2 atom % (i.e, 35 to 70 mass %) A Rh content of the sensor electrode relative to the whole of the Pt—Rh alloy of the sensor electrode is 44.8 to 77.9 atom % (i.e., 30 to 65 mass %). An atomic weight of Pt is 195.08 (g/mol). An atomic weight of Rh is 102.91 (g/mol).

When the Pt content is less than 35 mass %, in other words, the Rh content is greater than 65 mass %, the amount of oxygen adsorbed to Rh is high, thus resulting in a risk that the activation time of the sensor electrode is prolonged. There is also a risk that an oxidization-related expansion of Rh is great, which may cause detaching of the sensor electrode.

When the Pt content is greater than 70 mass %, in other words, the Rh content is less than 30 mass %, so that the amount of Rh is low, there is a risk that the NOx activity drops. There is also a risk that it is impossible to ensure limiting current characteristics, which leads to a decrease in measurement accuracy.

Rh usually has properties to easily adsorb NOx (nitrogen oxide) and $O_2$ (oxygen). An increase in the Rh content will result in an increase in ability thereof to adsorb NOx, which minimizes a change rate of oxygen ion current, as detected by the sensor electrode, which arises from a change in voltage applied to the sensor electrode. Alternatively, when the Rh content is undesirably high, it requires a lot of time to remove $O_2$ adsorbed to Rh when the NOx sensor is activated, thereby increasing the activation time of the sensor electrode. Rh in the sensor electrode which is contactable directly with NOx and $O_2$ is Rh arranged on the surface of the sensor electrode.

The NOx sensor is, therefore, engineered not only to define the ratio of Pt to Rh in the whole of the sensor electrode, but also to have the percentage of Rh in the Pt—Rh alloy of the surface layer of the sensor electrode which is higher than the percentage of Rh in the Pt—Rh alloy in the whole of the sensor electrode by an atomic composition percentage of 4 to 10 atom %. The surface of the sensor electrode has irregularities formed by the Pt—Rh alloy. The surface layer of the sensor electrode is defined by a portion of a thickness of the sensor electrode. Specifically, the surface layer is a portion of the sensor electrode ranging from the surface thereof to a depth of 350 nm in a thickness-wise direction perpendicular to a longitudinal center line of the sensor electrode, in other words, in a direction substantially perpendicular to the surface of the solid electrolyte body and also has an inner surface opposed to the outer surface of the surface layer. The outline of the inner surface is geometrically identical with, that is, contoured to conform with that of the outer surface of the surface layer. In other words, the surface layer is made of a portion of the sensor electrode which has a depth of 350 nm from the outer surface thereof.

The selection of the percentage of Rh in the surface layer of the sensor electrode to be higher than the percentage of Rh in the whole of the sensor electrode by an atomic composition percentage of 4 to 10 atom % serves to decrease the change rate of the oxygen ion current in the sensor electrode (which will also be referred to as a current change rate) and also to shorten the activation time of the sensor electrode.

It is noted that when the above difference of the percentage of Rh is less than 4 atom %, it becomes difficult to reduce the current change rate. Alternatively, when the difference of the percentage of Rh is greater than 10 atom %, it also becomes difficult to shorten the activation time.

The sensor electrode may contain metallic components other than Pt or Rh. For instance, in the case where the pump electrode is made of a Pt—Au alloy, Au may be evaporated and adhered to the sensor electrode when the NOx sensor is produced. In this case, the sensor electrode contains a small amount of Au in addition to the Pt—Rh alloy.

EMBODIMENTS FOR CARRYING OUT THE INVENTION

Figure 1:
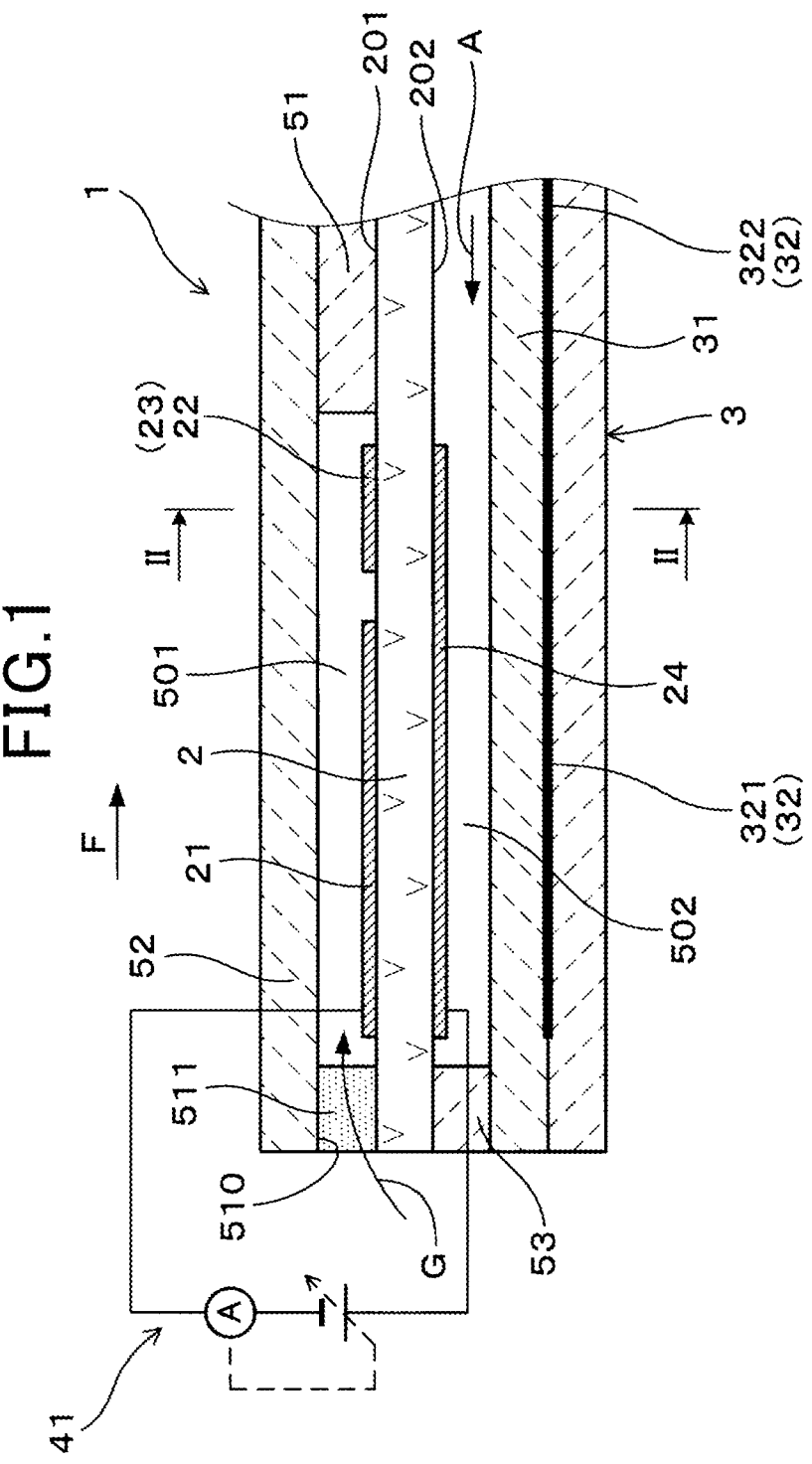
FIG. 1 is an explanatory sectional view which illustrates a NOx sensor according to an embodiment.

Embodiments of a NOx sensor will be described below. The NOx sensor is equipped with a sensor electrode. The sensor electrode contains Pt—Rh alloy and $ZrO_2$. The mass ratio of the Pt—Rh alloy to Zr in the whole of the sensor electrode is preferably selected to be Pt—Rh alloy:Zr=93:7 to 75:25. The percentage of Zr in the sum of the Pt—Rh alloy and Zr in the surface layer of the sensor electrode is preferably higher than the percentage of Zr in the sum of the Pt—Rh alloy and Zr in the whole of the sensor electrode by an atomic composition percentage of 25 to 55 atom %.

It is useful to define a ratio between the Pt—Rh alloy and Zr in the sensor electrode for minimizing the change rate of the oxygen ion current in the sensor electrode.

Specifically, the mass ratio of the Pt—Rh alloy to Zr (zirconium) in the whole of the sensor electrode is Pt—Rh alloy:Zr=93:7 to 75:25. The mass ratio is expressed in terms of an atomic composition percentage. When the mass ratio of Pt to Rh in the whole of the sensor electrode is Pt:Rh=70:30, the amount of the Pt—Rh alloy contained in the whole of the sensor electrode is 62.0 to 87.9 atom % (i.e., 75 to 93 mass %) of the whole of the sensor electrode. The amount of Zr contained in the whole of the sensor electrode is 12.1 to 38.0 atom % (i.e., 7 to 25 mass %) of the whole of the sensor electrode.

When the mass ratio of Pt to Rh in the whole of the sensor electrode is Pt:Rh=35:65, the amount of the Pt—Rh alloy contained in the whole of the sensor electrode is 66.9 to 90.0 atom % (i.e., 75 to 93 mass %) of the whole of the sensor electrode. In this case, the amount of Zr contained in the whole of the sensor electrode is 10.0 to 33.1 atom % (i.e., 7 to 25 mass %) of the whole of the sensor electrode.

The atomic weight of Zr is selected to be 91.22 (g/mol). The atomic composition ratio of Pt to Rh is 70:30. The atomic weight of the Pt—Rh alloy in the whole of the sensor electrode is selected to be 167.43 (g/mol). The atomic composition ratio of Pt to Rh is 35:65. The atomic weight of the Pt—Rh alloy in the whole of the sensor electrode is selected to be 135.17 (g/mol).

In a three-phase interface of the Pt—Rh alloy of the sensor electrode, $ZrO_2$ of the sensor electrode, and the measurement gas containing oxygen, the Pt—Rh ally adsorbs oxygen atoms in NOx, so that the oxygen atoms are ionized and then pass through $ZrO_2$ to create a flow of oxygen ion current. The surface layer of the sensor electrode has a large amount of Zr, thereby facilitating oxidization of oxygen atoms in NOx to enhance the ability to decompose NOx and decrease the current change rate in the sensor electrode.

When the percentage of Zr in the surface layer of the sensor electrode becomes undesirably high, it results in a decrease in percentage of the Pt—Rh alloy in the surface layer in the sensor electrode, which increases a conduction resistance thereof to adsorption of oxygen atoms in NOx, thus resulting in an increased difficulty in reducing the current change rate in the sensor electrode.

The percentage of Zr in the sum of the Pt—Rh alloy and Zr in the surface layer of the sensor electrode is, therefore, selected to be higher than the percentage of Zr in the sum of the Pt—Rh alloy and Zr in the whole of the sensor electrode by an atomic composition percentage of 25 to 55 atom %. This further decreases the current change rate in the sensor electrode.

When the above difference of the percentage of Zr is lower than 25 atom %, it becomes difficult to ionize oxygen atoms in NOx, thereby resulting in an increased difficulty in decreasing the current change rate in the sensor electrode. Alternatively, when the difference of the percentage of Zr is higher than 55 atom %, it becomes difficult to ensure the conductivity of the sensor electrode, thereby resulting in an increased difficulty in decreasing the current change rate in the sensor electrode.

The sensor electrode may contain $Y_2O_3$ (yttrium oxide or yttria) in addition to $ZrO_2$. $Y_2O_3$ may be used as a stabilizing agent to stabilize $ZrO_2$ into a cubical crystal or a tetragonal crystal. The amount of $Y_2O_3$ contained in ceramic components of the sensor electrode may be selected to be 5 to 10 mol %.

When the ceramic component of the sensor electrode is yttria-stabilized zirconia containing $ZrO_2$ and $Y_2O_3$, the mass ratio of Zr to the sum of the Pt—Rh alloy to Zr in the whole of the sensor electrode is identical with that when the sensor electrode has a ceramic component made of zirconia which does not contain yttria. Additionally a difference between the percentage of Zr in the whole of the sensor electrode made of yttria-stabilized zirconia and the percentage of Zr in the surface layer of the sensor electrode is identical with that when the sensor electrode has a ceramic component made of zirconia which does not contain yttria.

A reference electrode (24) is disposed on a surface (202) of the solid electrolyte body which is exposed to a reference gas (A) containing a constant concentration of oxygen. The reference electrode is opposed to the sensor electrode in a thickness-wise direction of the NOx sensor. The reference electrode contains Pt and $ZrO_2$. The mass ratio of Pt to Zr in the whole of the reference electrode is Pt:Zr=97:3 to 85:15. The percentage of Zr in the sum of Pt and Zr in a surface layer (241) of the reference electrode ranging from a surface (240) of the reference electrode to a depth of 350 nm is preferably higher than the percentage of Zr in the sum of Pt and Zr in the whole of the reference electrode by an atomic composition percentage of 40 to 65 atom %.

It is useful to specify components of the reference electrode which is disposed on the solid electrolyte body and opposed to the sensor electrode in order to enhance the ability to decompose NOx.

Specifically, the mass ratio of Pt to Zr in the whole of the reference electrode containing Pt and $ZrO_2$ is selected to be Pt:Zr=97:3 to 85:15. The mass ratio is expressed in terms of an atomic composition percentage. The amount of Pt contained in the whole of the reference electrode is selected to be 72.6 to 93.8 atom % (i.e., 85 to 97 mass %) of the whole of the reference electrode. The amount of Zr contained in the whole of the reference electrode is selected to be 6.2 to 27.4 atom % (i.e., 3 to 15 mass %) of the whole of the reference electrode.

In a three-phase interface of Pt of the reference electrode, $ZrO_2$ of the reference electrode, and the reference gas containing a constant concentration of oxygen, ionized oxygen atoms pass through $ZrO_2$ and then are changed into molecules at Pt. The surface layer of the reference electrode is richer in Zr, thereby facilitating the passage of the ionized oxygen atoms to enhance the ability to decompose NOx, which decreases the current change rate in the sensor electrode.

When the percentage of Zr in the surface layer of the reference electrode is undesirably increased, it results in a decrease in percentage of Pt in the surface layer of the sensor electrode, which increases the conduction resistance, thus resulting in an increased difficulty in decreasing the current change rate in the sensor electrode.

The decreasing of the current change rate in the sensor electrode is, therefore, achieved by selecting the percentage of Zr in the sum of Pt and Zr in the surface layer of the reference electrode to be higher than the percentage of Zr in the sum of Pt and Zr in the whole of the reference electrode by an atomic composition percentage of 40 to 65 atom %.

When the above difference of the percentage of Zr is less than 40 atom %, it becomes difficult for ionized oxygen atoms to pass through $ZrO_2$, thus resulting in an increased difficulty in decreasing the current change rate in the sensor electrode. Alternatively, when the difference of the percentage of Zr is greater than 65 atom %, it becomes difficult to ensure the conductivity of the reference electrode, thus resulting in an increased difficulty in decreasing the current change rate in the sensor electrode.

EMBODIMENT

The NOx sensor 1 of an embodiment will be described low with reference to the drawings.

Embodiment 1

Figure 2:
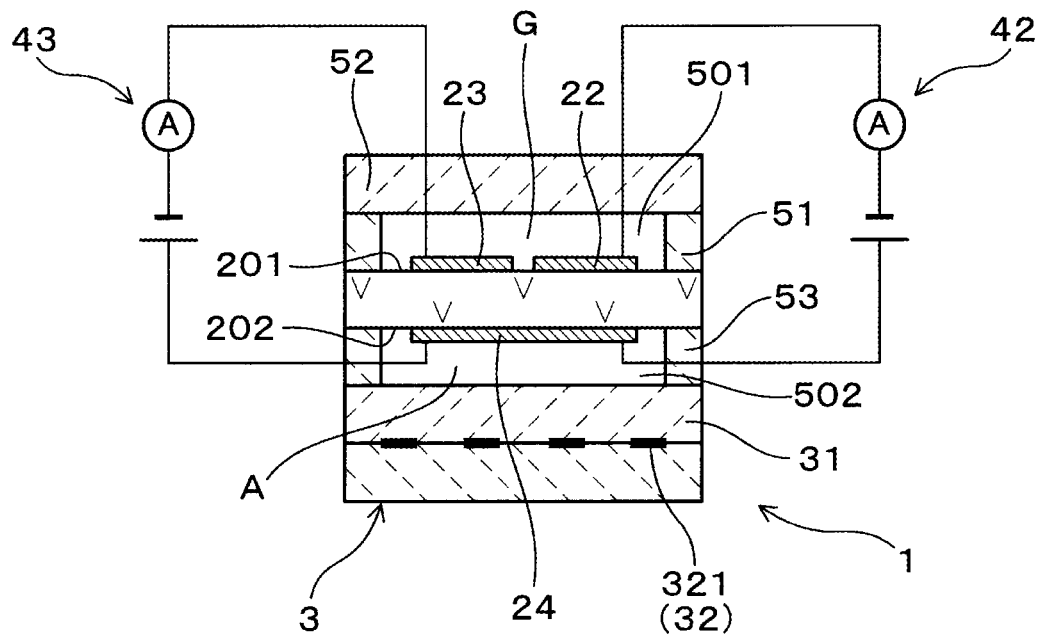
FIG. 2 is an explanatory sectional view, as taken along the line II-II in FIG. 1, which illustrates a NOx sensor according to an embodiment.

The NOx sensor 1 is, as illustrated in FIGS. 1 and 2, equipped with the solid electrolyte body 2, the pump electrode 21, and the sensor electrode 22. The solid electrolyte body 2 is of a plate-shape and has oxygen ion conductivity. The pump electrode 21 is mounted on the first surface 201 of the solid electrolyte body 2 which is exposed to the measurement gas G containing oxygen and used to regulate the oxygen concentration of the measurement gas G. The sensor electrode 22 is mounted on the first surface 201 of the solid electrolyte body 2 which is exposed to the measurement gas G for use in measuring the oxygen centration through the pump electrode 21.

A metallic component of the sensor electrode 22 is a Pt—Rh alloy. A mass ratio of Pt to Rh in the whole of the sensor electrode 22 is Pt:Rh=70:30 to 35:65. In other words, a Pt content of the sensor electrode 22 relative to the whole of the Pt—Rh alloy of the sensor electrode 22 is 22.1 to 55.2 atom % (i.e, 35 to 70 mass %) A Rh content of the sensor electrode 22 relative to the whole of the Pt—Rh alloy of the sensor electrode 22 is 44.8 to 77.9 atom % (i.e., 30 to 65 mass %).

The percentage of Rh in the Pt—Rh alloy of the surface layer 221 ranging from the outer surface 220 of the sensor electrode 22 to a depth of 350 nm is higher by 4 to 10 atom % in terms of atomic composition percentage than the percentage of Rh in the Pt—Rh alloy over the whole of the sensor electrode 22.

The NOx sensor 1 will be described below in detail with reference to FIGS. 1 to 19.

The NOx sensor 1 is used in an exhaust pipe of an automotive vehicle. The measurement gas G is exhaust gas passing through the exhaust pipe. The NOx sensor 1 is used for measuring the concentration of NOx (i.e., nitrogen oxide) that is a given gas component contained in the exhaust gas.

The NOx sensor 1 is retained by a housing through an insulator. The housing is secured to the exhaust pipe. The NOx sensor 1 has a front portion which protrudes from the insulator and is covered with a protective cover which has formed therein through-holes through which the measurement gas G passes.

The monitor electrode 23 is, as illustrated in FIGS. 1 and 2, disposed on the first surface 201 of the solid electrolyte body 2 at an interval away from the sensor electrode 22 in the width-wise direction of the solid electrolyte body 2. The monitor electrode 23 is used to detect the oxygen concentration of the measurement gas G after being regulated in oxygen concentration thereof by the pump electrode 21.

The reference electrode 24 is mounted on the second surface 202 of the solid electrolyte body 2 which is exposed to air as reference gas A. The reference electrode 24 on the second surface 202 faces the pump electrode 21, the sensor electrode 22, and the monitor electrode 23 attached to the first surface 201 of the solid electrolyte body 2 in the thickness-wise direction of the solid electrolyte body 2. The reference electrode 24 is made of a single electrode and may be located so as to fully coincide with an area of the solid electrolyte body 2 on which the pump electrode 21, the sensor electrode 22, and the monitor electrode 23 are disposed in the thickness-wise direction of the solid electrolyte body 2. The reference electrode 24 may be made of a plurality of discrete electrodes each of which faces one of the pump electrode 21, the sensor electrode 22, and the monitor electrode 23 in the thickness-wise direction of the solid electrolyte body 2.

The pump electrode 21, the sensor electrode 22, the monitor electrode 23, and the reference electrode 24 are arranged on the single solid electrolyte body 2. The insulator 52 which is plate-like is stacked on the first surface 201 of the solid electrolyte body 2 through the spacer 51. On the first surface 201 of the solid electrolyte body 2, the gas chamber 501 into which the gas measurement gas G is introduced is defined by the solid electrolyte body 2, the spacer 51, and the insulator 52. The hole 510 formed in the spacer 51 has disposed therein the diffusion resistance layer 511 through which the measurement gas G is admitted into the gas chamber 501 while being subjected to a given diffusion resistance. The heater 3 which is of a plate shape is stacked on the second surface 202 of the solid electrolyte body 2 through the spacer 53. On the second surface 202 of the solid electrolyte body 2, the reference gas chamber 502 into which the reference gas A is admitted is defined by the solid electrolyte body 2, the spacer 53, and the heater 3.

In the NOx sensor 1, the pump cell 41 is, as illustrated in FIG. 1, formed by the pump electrode 21, the reference electrode 24 (in this embodiment, a portion of the reference electrode 24), and a portion of the solid electrolyte body 2 disposed between the pump electrode 21 and the reference electrode 24. The pump cell 41 works to remove oxygen from the measurement gas G by applying voltage between the pump electrode 21 and the reference electrode 24 to create a flow of oxygen ion current between the pump electrode 21 and the reference electrode 24.

In the NOx sensor 1, the sensor cell 42 is, as illustrated in FIG. 2, formed by the sensor electrode 22, the reference electrode 24 (in this embodiment, a portion of the reference electrode 24), and a portion of the solid electrolyte body 2 arranged between the sensor electrode 22 and the reference electrode 24. The sensor cell 42 works to measure the oxygen ion current flowing between the sensor electrode 22 and the reference electrode 24 when the voltage is being applied to the sensor electrode 22 and the reference electrode 24.

In the NOx sensor 1, the monitor cell 43 is formed by the monitor electrode 23, the reference electrode 24 (in this embodiment, a portion of the reference electrode 24), and a portion of the solid electrolyte body 2 arranged between the monitor electrode 23, the reference electrode 24. The monitor cell 43 works to measure the oxygen ion current flowing between the monitor electrode 23 and the reference electrode 24 when the voltage is being applied between the monitor electrode 23 and the reference electrode 24.

The sensor cell 42 serves to measure the oxygen ion current produced by NOx and residual oxygen. The monitor cell 43 works to measure the oxygen ion current arising from the residual oxygen. The value of the oxygen ion current measured by the monitor cell 43 is subtracted from that produced by the sensor cell 42 to derive the concentration of NOx in the measurement gas G.

The heater 3 is, as illustrated in FIGS. 1 and 2, made up of a pair of insulating heater substrates 31 and the conductive layer 32 disposed on the heater substrates 31. The conductive layer 32 is equipped with a pair of leads 322 and the heating body 321 which connects the leads 322 together. The heating body 321 is smaller in sectional area than the leads 322, so that the heating body 321 will produce a greater amount of Joule heat than that produced by the leads 322 when the current is delivered between the leads 322.

The heater substrate 31, the insulator 52, and the spacers 51 and 53 are made from ceramic such as alumina. The conductive layer 32 is interposed between the heater substrates 31 and made of a conductive layer of a constant thickness arranged on the heater substrates 31.

The NOx sensor 1 of this embodiment specifies compositions of the surface layer 221 of the sensor electrode 22 (i.e., a layer from the surface 220 to a depth of 350 nm) for use in measuring the concentration of NOx in the measurement gas G.

Specifically, a percentage of Rh contained in the Pt—Rh alloy of the surface layer 221 of the sensor electrode 22 is higher than that of Rh contained in the Pt—Rh alloy of the whole of the sensor electrode 22. Additionally, the sensor electrode 22 contains $ZrO_2$ and $Y_2O_3$ in addition to the Pt—Rh alloy.

Figure 3:
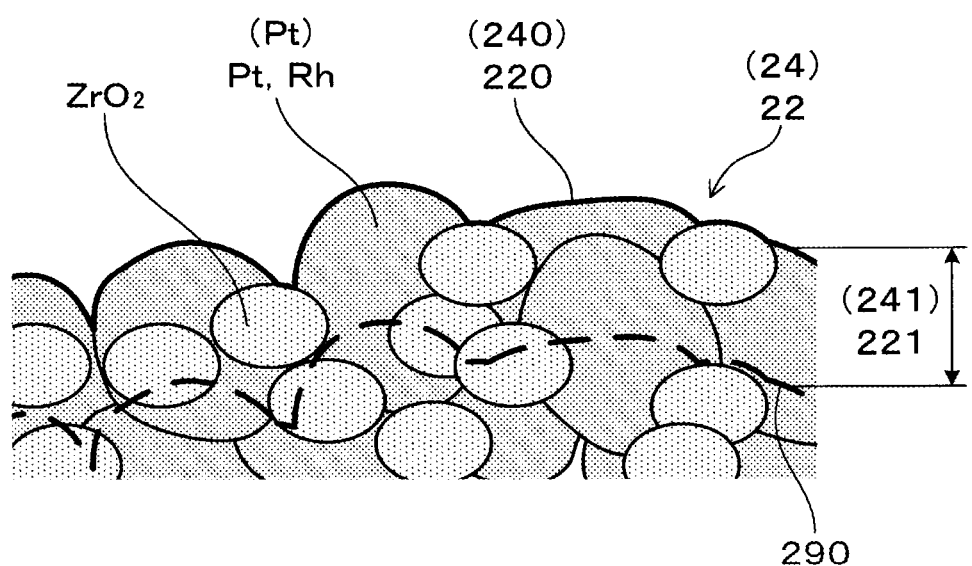
FIG. 3 is a schematic view which illustrates a surface layer of a sensor electrode according to an embodiment.

FIG. 3 schematically illustrates a region around the surface layer 221 of the sensor electrode 22. In the whole of the sensor electrode 22, metallic particles of Pt and Rh whose grain diameter is 0.8 to 3 μm and ceramic particles of $ZrO_2$ (containing $Y_2O_3$) whose grain diameter is 0.5 to 2.5 μm are mixed. On the surface 220 of the sensor electrode 22, irregularities exist which are formed by the metallic particles of Pt and Rh and the ceramic particles of $ZrO_2$. The surface layer 221 of the sensor electrode 22 forms a portion of thickness of the sensor electrode 22. Specifically, the surface layer 221 is a portion of the sensor electrode 22 ranging from the surface 220 to a depth of 350 nm in a thickness-wise direction perpendicular to a longitudinal center line of the sensor electrode 22, in other words, in a direction substantially perpendicular to the surface 201 of the solid electrolyte body 2 and also has an inner surface 290 facing the surface 220 of the surface layer 221. The outline of the inner surface 290 is geometrically identical with, that is, contoured to conform with that of the surface 220. In other words, the surface layer 221 is made of a portion of the sensor electrode 22 which has a depth of 350 nm from the surface 220. A difference in atomic composition ratio between Pt and Rh in the surface layer 221 of the sensor electrode 22 is expressed as a difference between the percentage of a surface area of Pt appearing on the surface 220 of the sensor electrode 22 in an entire area of the surface 220 and the percentage of a surface area of Rh appearing on the surface 220 of the sensor electrode 22 in the entire area of the surface 220. Pt and Rh are contained in the metallic particles in the form of an alloy.

In this embodiment, as an index representing the performance of the sensor electrode 22, a rate of change in oxygen ion current I (i.e., a current change rate X) in the sensor electrode 22 and an activation time T of the sensor electrode 22 are used. The current change rate X and the activation time T are an index associated with the ability of the NOx sensor 1 to decompose NOx.

Figure 4:
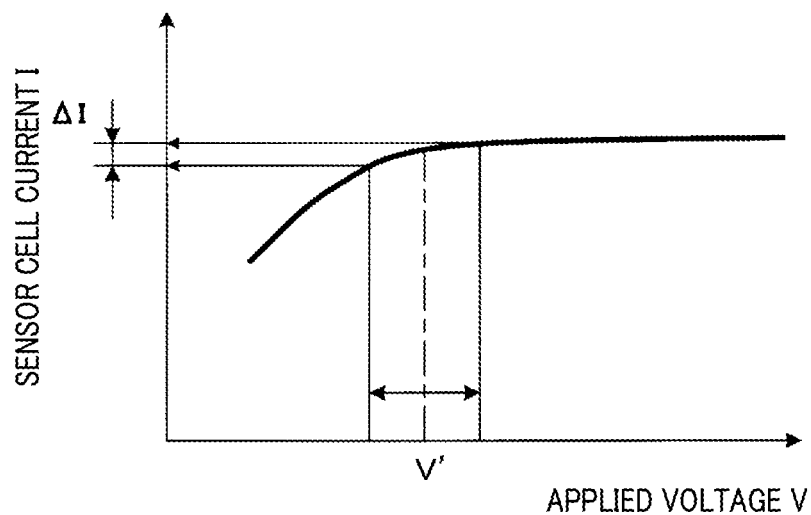
FIG. 4 is a graph which represents a relation between voltage applied to a sensor cell and a sensor cell current according to an embodiment.

FIG. 4 represent a relation between the voltage V applied to the sensor cell 42 (i.e., voltage between the sensor electrode 22 and the reference electrode 24) and oxygen ion current I flowing through the sensor cell 42 (which will also be referred to as sensor cell current I). The voltage V applied to the sensor cell 42 is defined as voltage V' which indicates limiting current characteristics in which the oxygen ion current flowing through the sensor cell 42 is kept substantially constant regardless of a change in the voltage. The current change rate X is expressed by a rate of change in sensor cell current I resulting from a change in voltage V' of ±0.01 V according to an equation of $X=\Delta I/(2 \cdot I) \times 100 (\%)$.

Figure 5:
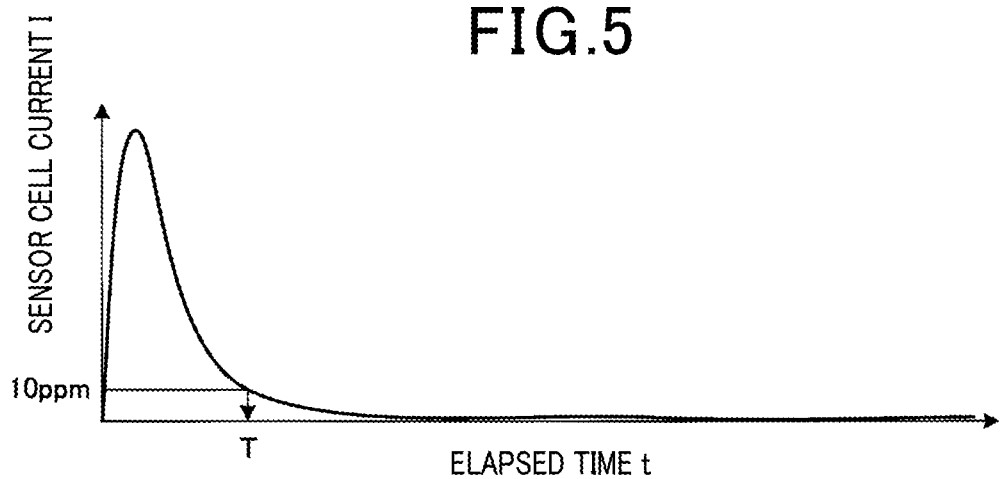
FIG. 5 is a graph which represents a relation between a time elapsed from when a NOx sensor is activated and a sensor cell current according to an embodiment.

FIG. 5 represents a relation between an elapsed time t from activation of the NOx sensor 1 and the sensor cell current I. When the gas chamber 501 is in the atmospheric state immediately after the NOx sensor 1 is activated, oxygen adsorbed to Rh of the surface 220 of the sensor electrode 22 is emitted, so that the sensor cell current I temporarily becomes much larger. The activation time T is expressed by a time interval between when the NOx sensor 1 starts to be activated (i.e., the heater 3 starts to be energized) and when the concentration of NOx, as indicated by the sensor cell current I, drops below 10 ppm.

Figure 6:
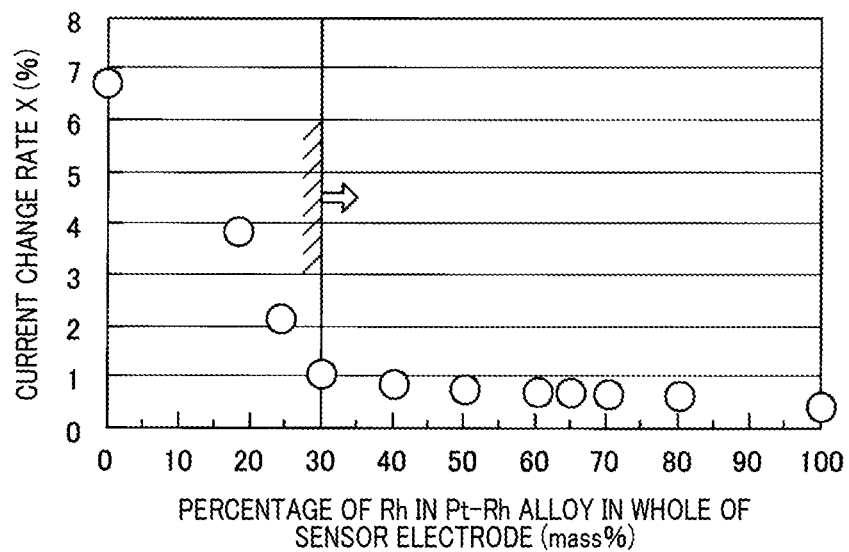
FIG. 6 is a graph which represents a relation between a percentage (mass %) of Rh contained in a Pt—Rh alloy in the whole of a sensor electrode and a current change rate (%) according to an embodiment.

FIG. 6 represents a relation between the percentage (i.e., mass %) of Rh contained in the Pt—Rh alloy in the whole of the sensor electrode 22 and the current change rate X (%). The graph of FIG. 6 shows that when the percentage of Rh is decreased below 30 mass %, the current change rate X increases. This is because a decrease in percentage of Rh in the whole of the sensor electrode 22 results in a decrease in ability of Rh to adsorb NOx and $O_2$.

Figure 7:
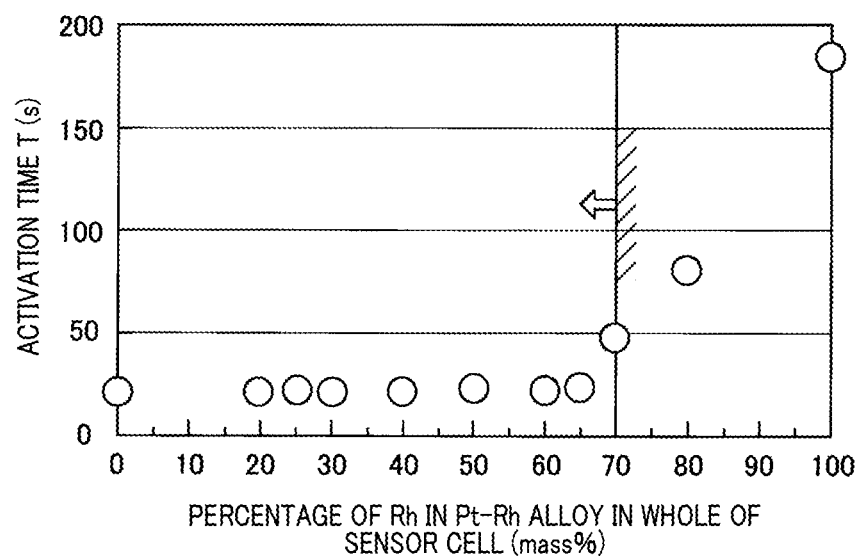
FIG. 7 is a graph which represents a relation between a percentage (mass %) of Rh contained in a Pt—Rh alloy in the whole of a sensor electrode and an activation time (s) according to an embodiment.

FIG. 7 represents a relation between the percentage (i.e., mass %) of Rh contained in the Pt—Rh alloy in the whole of the sensor electrode 22 and the activation time T(s) and shows that when the percentage of Rh is increase above 65 mass %, the activation time T becomes long. This is because an increase in percentage of Rh in the whole of the sensor electrode 22 results in an increase in time required to remove $O_2$ adsorbed to Rh when the NOx sensor 1 is activated.

Figure 8:
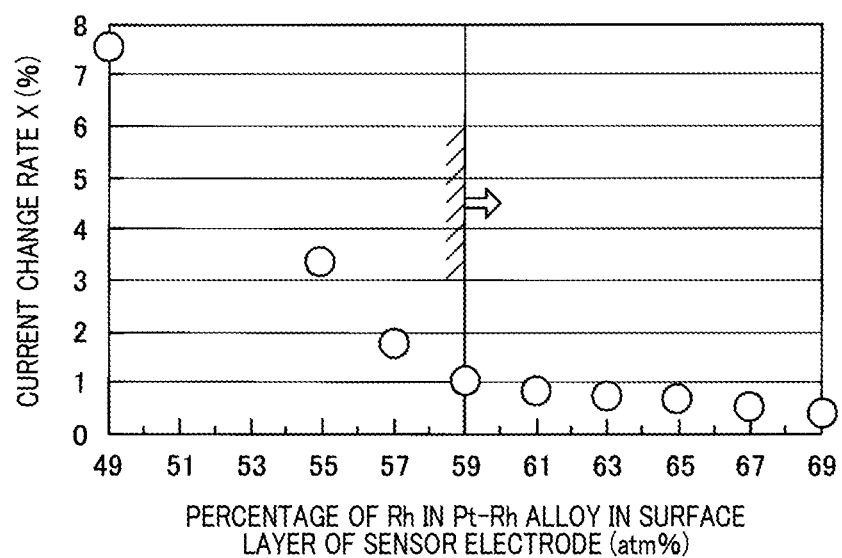
FIG. 8 is a graph which represents a relation between a percentage (atom %) of Rh contained in a Pt—Rh alloy in a surface layer of a sensor electrode and a current change rate (%) according to an embodiment.

FIG. 8 represents a relation between the percentage (i.e., atom %) of Rh contained in the Pt—Rh alloy in the surface layer 221 of the sensor electrode 22 and the current change rate X (%). The ratio of mass of Pt to mass of Rh in the whole of the sensor electrode 22 is selected to be Pt:Rh=60:40. In this case, the amount of Rh entirely contained in the Pt—Rh alloy of the sensor electrode 22 is 55 atom %. When the percentage of Rh in the surface layer 221 is decreased below 59 atom %, the current change rate X will increase. This is because a decrease in percentage of Rh in the surface layer 221 will result in a decrease in ability of Rh to adsorb NOx and $O_2$.

Figure 9:
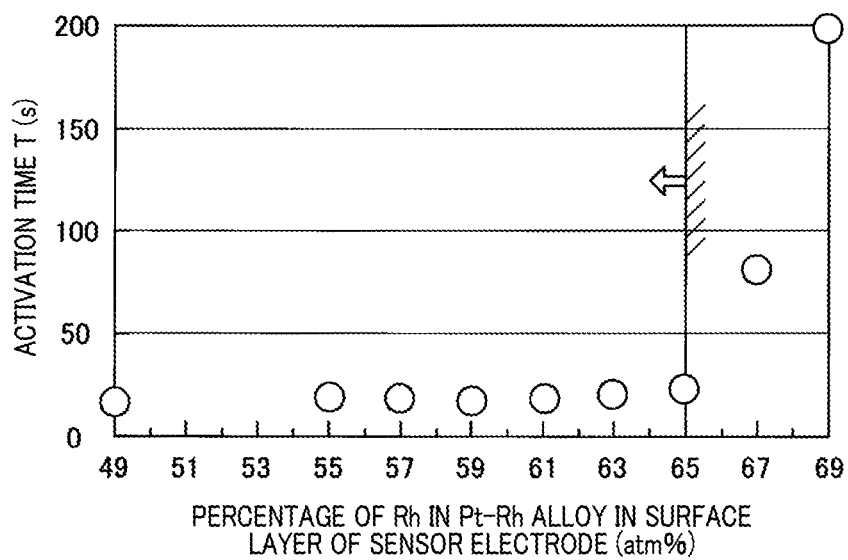
FIG. 9 is a graph which represents a relation between a percentage (atom %) of Rh contained in a Pt—Rh alloy in a surface layer of a sensor electrode and an activation time (s) according to an embodiment.

FIG. 9 represents a relation between the percentage (i.e., atom %) of Rh contained in the Pt—Rh alloy in the surface layer 221 of the sensor electrode 22 and the activation time T(s). The ratio of mass of Pt to mass of Rh in the whole of the sensor electrode 22 is selected to be Pt:Rh=60:40. In this case, the amount of Rh entirely contained in the Pt—Rh alloy of the sensor electrode 22 is 55 atom %. When the percentage of Rh in the surface layer 221 is increased above 65 atom %, the activation time T becomes long. This is because an increase in percentage of Rh in the surface layer 221 will result in an increase in time required to remove $O_2$ adsorbed to Rh when the NOx sensor 1 is activated.

The graphs of FIGS. 8 and 9 show that decreases in the current change rate X in the sensor electrode 22 and also in the activation time T are achieved by increasing the percentage of Rh contained in the Pt—Rh alloy in the surface layer 221 of the sensor electrode 22 to be greater than the percentage of Rh contained in the Pt—Rh alloy in the whole of the sensor electrode 22 by an atomic composition percentage of 4 to 10 atom %.

The NOx sensor 1 of this embodiment is designed to have the ratio of mass of the Pt—Rh alloy to mass of Zr in the whole of the sensor electrode 22 which is selected to be Pt—Rh alloy:Zr=93:7 to 75:25. Additionally, the percentage of Zr in the sum of the Pt—Rh alloy and Zr contained in the surface layer 221 of the sensor electrode 22 is higher than the percentage of Zr in the sum of the Pt—Rh alloy and Zr in the whole of the sensor electrode 22 by an atomic composition percentage of 25 to 55 atom %.

The ceramic component in the sensor electrode 22 is yttria-stabilized zirconia containing $ZrO_2$ and $Y_2O_3$.

Figure 10:
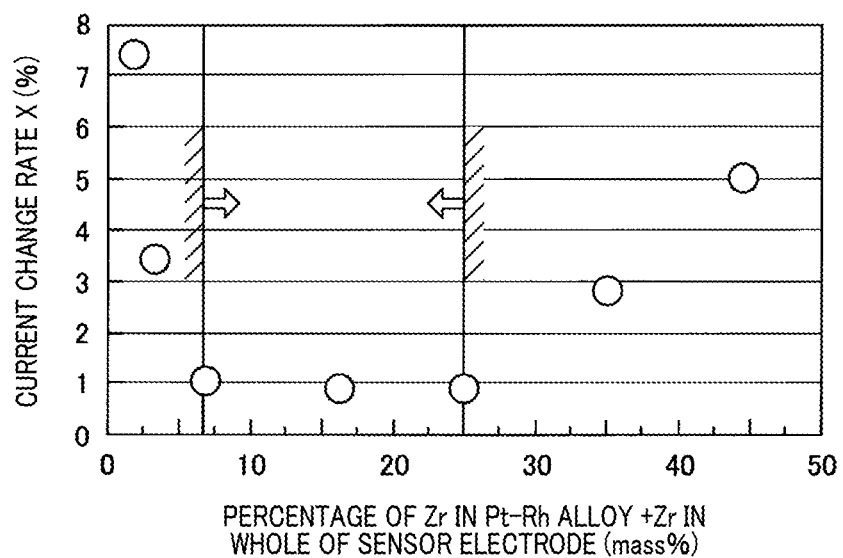
FIG. 10 is a graph which represents a relation between a percentage (mass %) of Zr in the sum of a Pt—Rh alloy and Zr in the whole of a sensor electrode and a current change rate (%) according to an embodiment.

FIG. 10 represents a relation between the percentage (i.e., mass %) of Zr in the sum of the Pt—Rh alloy and Zr in the whole of the sensor electrode 22 and the current change rate X (%).

When the percentage of Zr is decreased below 7 mass %, the current change rate X increases. This is because a decrease in percentage of Zr in the whole of the sensor electrode 22 will result in a decrease in ability of $ZrO_2$ to facilitate ionization of oxygen atoms contained in NOx to decompose NOx. When the percentage of Zr is increased above 25 mass %, the current change rate X also increases. This is because an increase in percentage of Zr in the sensor electrode 22 will result in a decrease in percentage of the Pt—Rh alloy in the sensor electrode 22, which increases a conduction resistance thereof to adsorption of oxygen atoms in NOx.

Figure 11:
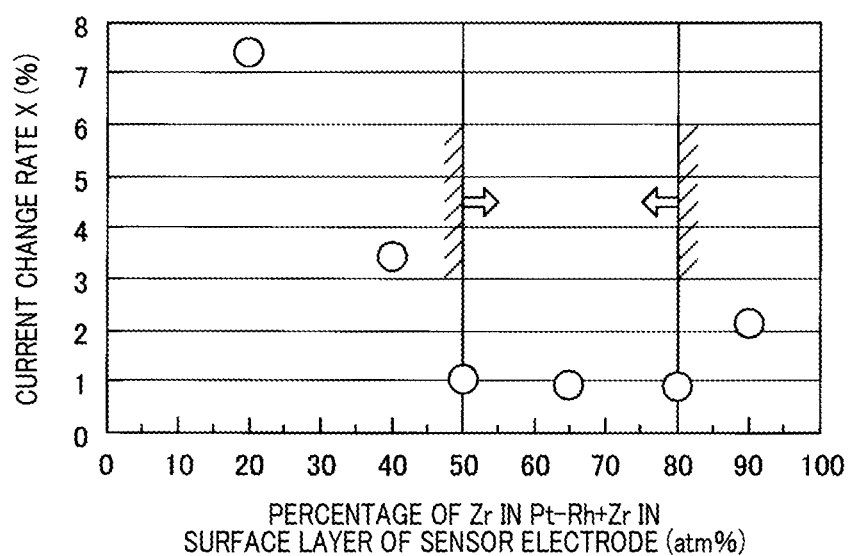
FIG. 11 is a graph which represents a relation between a percentage (atom %) of Zr in the sum of a Pt—Rh alloy and Zr in a surface layer of a sensor electrode and a current change rate (%) according to an embodiment.

FIG. 11 represents a relation between the percentage (i.e., mass %) of Zr in the Pt—Rh alloy and Zr in the surface layer 221 of the sensor electrode 22 and the current change rate X (%). The ratio of mass of Pt to mass of Rh in the whole of the sensor electrode 22 is selected to be Pt:Rh=60:40. The ratio of mass of the Pt—Rh alloy to mass of Zr in the whole of the sensor electrode 22 is selected to be Pt—Rh alloy:Zr=84:16. In this case, the amount of Zr contained in the sum of the Pt—Rh alloy and Zr in the sensor electrode 22 is 25 atom %.

When the percentage of Zr in the surface layer 221 of the sensor electrode 22 is decreased below 50 atom %, the current change rate X will increase. This is because a decrease in percentage of Zr in the surface layer 221 of the sensor electrode 22 will result in a decrease in ability of $ZrO_2$ to accelerate ionization of oxygen atoms in NOx to decompose NOx.

Alternatively, when the percentage of Zr in the surface layer 221 of the sensor electrode 22 is increased above 80 atom %, the current change rate X will slightly increase. This is because an increase in percentage of Zr in the surface layer 221 of the sensor electrode 22 will result in a decrease in percentage of the Pt—Rh alloy in the surface layer 221 of the sensor electrode 22, which increases the conduction resistance thereof to adsorption of oxygen atoms in NOx.

The graph of FIG. 11 shows that a decrease in the current change rate X in the sensor electrode 22 is achieved by increasing the percentage of Zr contained in the sum of the Pt—Rh alloy and Zr in the surface layer 221 of the sensor electrode 22 to be greater than the percentage of Zr contained in the sum of the Pt—Rh alloy and Zr in the whole of the sensor electrode 22 by an atomic composition percentage of 25 to 55 atom %.

The reference electrode 24 of the NOx sensor 1 in this embodiment contains Pt, $ZrO_2$, and $Y_2O_3$. The ratio of mass of Pt to mass of Zr in the whole of the reference electrode 24 is selected to be Pt:Zr=97:3 to 85:15. Additionally, the percentage of Zr in the sum of Pt and Zr contained in the surface layer 241 ranging from the surface 240 of the reference electrode 24 to a depth of 350 nm is higher than the percentage of Zr in the sum of Pt and Zr in the whole of the reference electrode 24 by an atomic composition percentage of 40 to 65 atom %. The ceramic component in the reference electrode 24 is yttria-stabilized zirconia containing $ZrO_2$ and $Y_2O_3$. The surface layer 241 of the reference electrode 24, like the surface layer 221 of the sensor electrode 22 in FIG. 3, ranges from the uneven surface 240 to a location whose depth is 350 nm and which is contoured to conform with the outline of the uneven surface 240. In FIG. 3, reference numerals or a symbol in parentheses are used for the reference electrode 24.

The pump electrode 21 and the monitor electrode 23 may be made of a Pt—Au alloy and $ZrO_2$.

Figure 12:
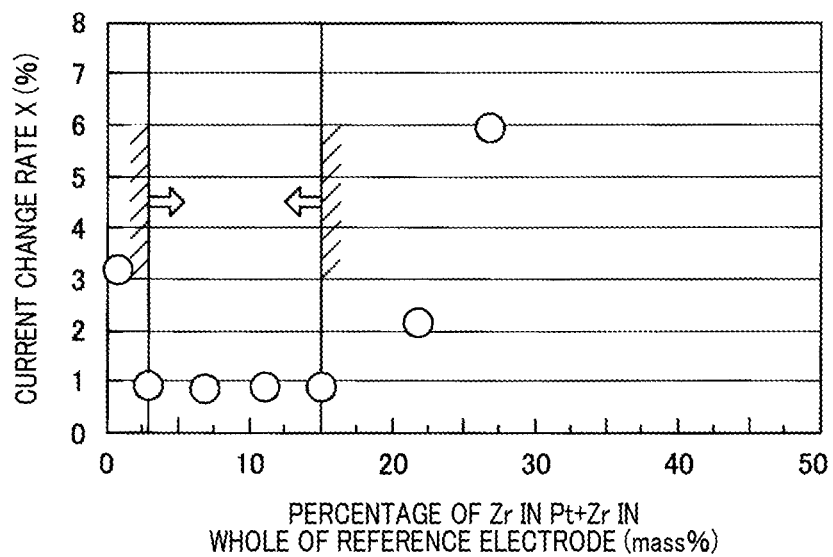
FIG. 12 is a graph which represents a relation between a percentage (mass %) of Zr in the sum of a Pt—Rh alloy and Zr in the whole of a reference electrode and a current change rate (%) according to an embodiment.

FIG. 12 represents a relation between the percentage of Zr (i.e. a mass %) in the sum of Pt and Zr in the whole of the reference electrode 24 and the current change rate X (%).

It is found that when the percentage of Zr is decreased below 3 mass %, it will result in an increase in the current change rate X. This is because it becomes difficult for oxygen atoms ionized by the sensor electrode 22 to pass through $ZrO_2$ in the reference electrode 24, thus resulting in a decrease in ability to decompose NOx. Additionally, when the percentage of Zr is increased above 15 mass %, it also result in an increase in the current change rate X. This is because an increase in percentage of Zr in the surface layer 241 of the reference electrode 24 will result in a decrease in percentage of Pt in the reference electrode 24, which increases a conduction resistance of the reference electrode 24.

Figure 13:
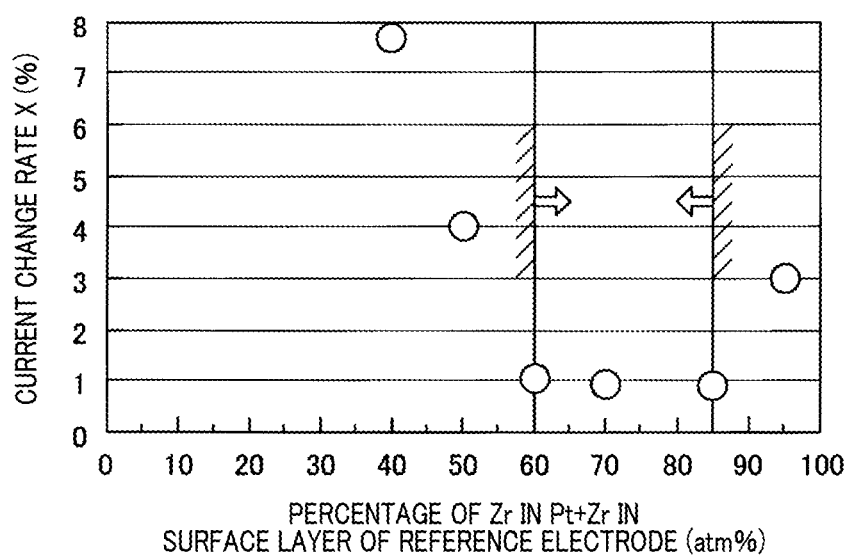
FIG. 13 is a graph which represents a relation between a percentage (atom %) of Zr in the sum of Pt and Zr in a surface layer of a reference electrode and a current change rate (%) according to an embodiment.

FIG. 13 represents a relation between the percentage of Zr (i.e. a mass %) in the sum of Pt and Zr in the surface layer 241 of the reference electrode 24 and the current change rate X (%). The ratio of mass of Pt to mass of Zr in the whole of the reference electrode 24 is selected to be Pt:Zr=90:10. In this case, the amount of Zr contained in the sum of Pt and Zr of the reference electrode 24 is 20 atom %.

When the percentage of Zr in the surface layer 241 of the reference electrode 24 is decreased below 60 atom %, it will result in an increase in the current change rate X. This is because it becomes difficult for oxygen atoms ionized by the sensor electrode 22 to pass through $ZrO_2$ in the surface layer 241 of the reference electrode 24, thereby resulting in a decrease in ability to decompose NOx.

Alternatively, when the percentage of Zr in the surface layer 241 of the reference electrode 24 is increased above 85 atom %, it will cause the current change rate X to slightly increase. This is because an increase in percentage of Zr in the surface layer 241 of the reference electrode 24 will result in a decrease in percentage of Pt in the surface layer 241 of the reference electrode 24, which increases the conduction resistance of the reference electrode 24.

The graph of FIG. 13 shows that a decrease in the current change rate X in the sensor electrode 22 is achieved by selecting the percentage of Zr contained in the sum of Pt and Zr in the surface layer 241 of the reference electrode 24 to be greater than the percentage of Zr in the sum of Pt and Zr in the whole of the reference electrode 24 by an atomic composition percentage of 40 to 65 atom %.

A method of producing the NOx sensor 1 of this embodiment will be described below.

First, the plate-like solid electrolyte body 2 on which the electrodes 21, 22, 23, and 24 are disposed, the plate-like insulator 52, the spacers 51 and 53, and the heater 3 are stacked to make a stacked body of the NOx sensor 1. Next, the stacked body is defatted in the atmospheric state to remove resin components from the stacked body. Subsequently, the stacked body is fired in circumstances where the oxygen concentration is decreased. The oxygen concentration during such firing is regulated to be lower than or equal to 3%, so that Rh contained in the Pt—Rh alloy of the sensor electrode 22 is attracted to oxygen, thereby avoiding the concentration of Rh around the surface 220 of the sensor electrode 22.

Figure 14:
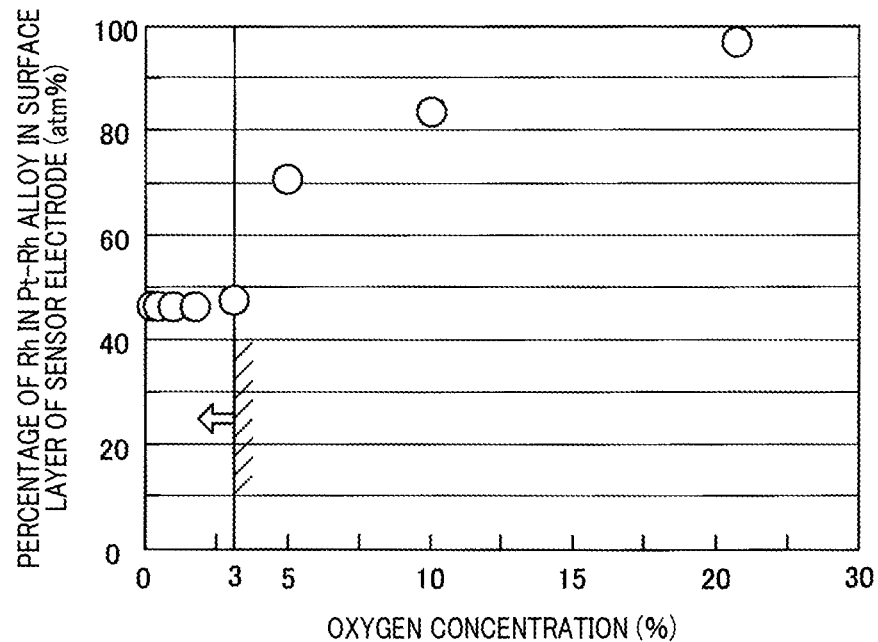
FIG. 14 is a graph which represents a relation between an oxygen concentration (%) in a firing operation and a percentage (atom %) of Rh contained in a Pt—Rh alloy in a surface layer of a sensor electrode according to an embodiment.

FIG. 14 represents a relation between the oxygen concentration (%) and the percentage (i.e., the mass %) of Rh contained in the Pt—Rh alloy in the surface layer 221 of the sensor electrode 22 in the firing operation. In this case, an atomic composition ratio of Pt to Rh contained in the Pt—Rh alloy in the whole of the sensor electrode 22 is selected to be Pt:Rh=45:55. In FIG. 14, when the firing operation is made in environments where the oxygen concentration is lower than or equal to 3%, the percentage of Rh contained in the Pt—Rh alloy in the surface layer 221 of the sensor electrode 22 is almost equal to the percentage of Rh contained in the Pt—Rh alloy in the whole of the sensor electrode 22.

Alternatively, when the oxygen concentration is greater than 3% in the firing operation, the percentage of Rh contained in the Pt—Rh alloy in the surface layer 221 of the sensor electrode 22 will increase. This is because an increase in oxygen concentration in the firing operation will cause Rh contained in the Pt—Rh alloy to be attracted to oxygen, so that it concentrates around the surface 220 of the sensor electrode 22.

The surface energy of Pt ($J/m^2$) is substantially identical with that of Rh. This causes the surface layer 211 whose compositions are substantially identical with those of material of the surface layer 211 when prepared to be formed as long as the oxygen concentration that is an external factor is kept low in the firing operation. This facilitates the ease with which final compositions of the surface layer 221 of the sensor electrode 22 are regulated.

After fired, the stacked body of the NOx sensor 1 is retained by an insulator. A trap layer is applied to a front end portion of the NOx sensor 1 and then burned. The trap layer is made of porous ceramic material and serves to avoid entry of electrode-poisoning substance into the gas chamber 501 of the NOx sensor 1.

Figure 15:
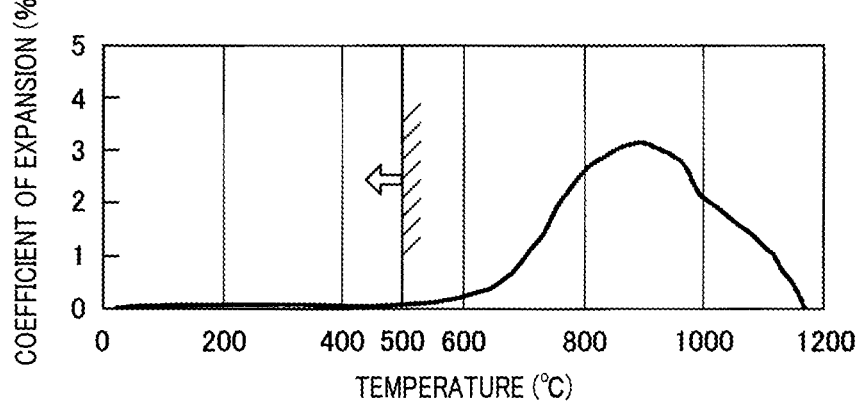
FIG. 15 is a graph which represents a relation of a temperature (° C.) at which a stacked body of a NOx sensor is heated and a coefficient of expansion (%) of a sensor electrode according to an embodiment.

FIG. 15 represents a relation between the temperature (° C.) at which the stacked body of the NOx sensor 1 is heated and the coefficient of expansion (i.e., the coefficient of linear expansion %) of the sensor electrode 22. In this case, an atomic composition ratio of Pt to Rh contained in the Pt—Rh alloy in the whole of the sensor electrode 22 is Pt:Rh=45:55. In FIG. 15, when the temperature is lower than or equal to 500° C., the sensor electrode 22 hardly expands. When the temperature is in a range of 500° C. to 1150° C., the sensor electrode 22 expands. The expansion of the sensor electrode 22 is thought of as arising from oxidization of Rh.

Therefore, when the stacked body of the NOx sensor 1 is heated in environments, such as the atmospheric state, where the oxygen concentration is high, the heating temperature is preferably regulated to be 500° C. or less. When the temperature at which the stacked body is exposed to air after being fired or the trap layer is burned is preferably regulated to be 500° C. or less.

After the trap layer is formed on the stacked body of the NOx sensor 1, regulating voltage V1 is applied to the sensor cell 42 (i.e., between the sensor electrode 22 and the reference electrode 24) to regulate compositions of the sensor electrode 22. The application of the regulating voltage V1 causes the percentage of Rh in the Pt—Rh alloy in the surface layer 221 of the sensor electrode 22 to be higher than the percentage of Rh in the Pt—Rh alloy in the whole of the sensor electrode 22.

The stacked body of the NOx sensor 1 which has been fired and on which the trap layer is burned is exposed to the atmosphere. Rh in the Pt—Rh alloy in the surface layer 221 of the sensor electrode 22 is then attracted to oxygen in the atmosphere, which may cause the percentage of Rh to be higher than a target value. The regulating voltage V1 which is higher than the voltage V' applied to the sensor cell 42 when the NOx sensor 1 is used is, therefore, applied to the sensor cell 42.

Figure 16:
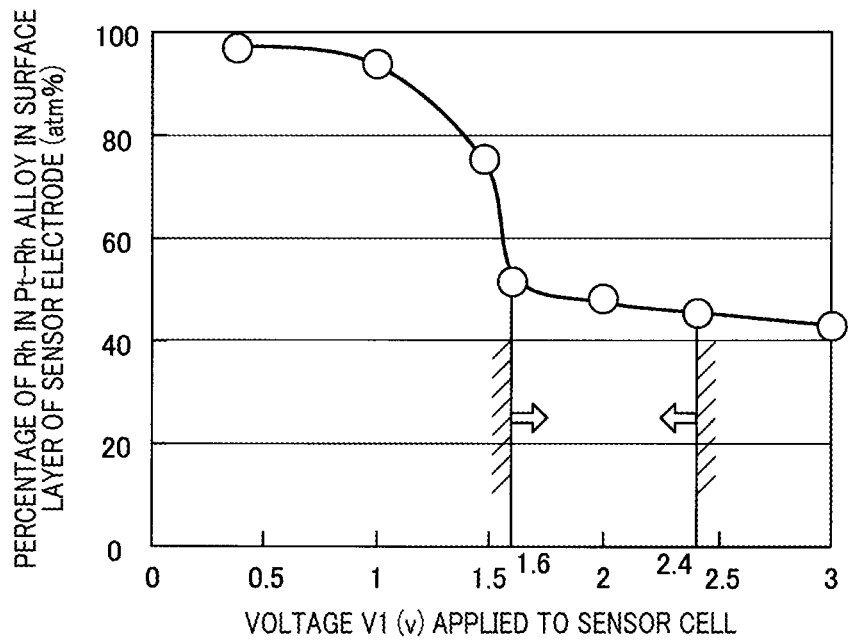
FIG. 16 is a graph which represents a voltage (V) applied to a sensor cell and a percentage (atom %) of Rh contained in a Pt—Rh alloy in a surface layer of a sensor electrode according to an embodiment.

FIG. 16 represents a relation between the regulating voltage V1(V) applied to the sensor cell 42 and the percentage (atom %) of Rh contained in the Pt—Rh alloy in the surface layer 221 of the sensor electrode 22. An atomic composition ratio of Pt to Rh in the Pt—Rh alloy in the whole of the sensor electrode 22 is Pt:Rh=45:55. An example where the regulating voltage V1 is applied in environments where the oxygen concentration is 100 ppm is shown.

FIG. 16 shows that when the regulating voltage V1 applied to the sensor cell 42 is less than as low as 1.6V, it is difficult to decrease the percentage of Rh in the Pt—Rh alloy in the surface layer 221 of the sensor electrode 22.

When the regulating voltage V1 is in a range of 1.6 to 2.4V, the percentage of Rh in the Pt—Rh alloy in the surface layer 221 of the sensor electrode 22 drops to a target value. This is because the application of the voltage V1 will result in a drop in oxygen concentration on the surface of the sensor electrode 22, so that Rh is diffused inside the surface since the surface energy of Pt is, as described above, substantially identical with that of Rh.

The application of the regulating voltage V1 which is higher than 2.4V to the sensor cell 42, however, causes $O_2$ to be strongly removed from $ZrO_2$ in the sensor electrode 22, which leads to a risk that the crystal structure of $ZrO_2$ is broken. This may result in defects of the NOx sensor 1.

It is, therefore, advisable that the regulating voltage V1 applied to the sensor cell 42 be in a range of 1.6 to 2.4V.

Figure 17:
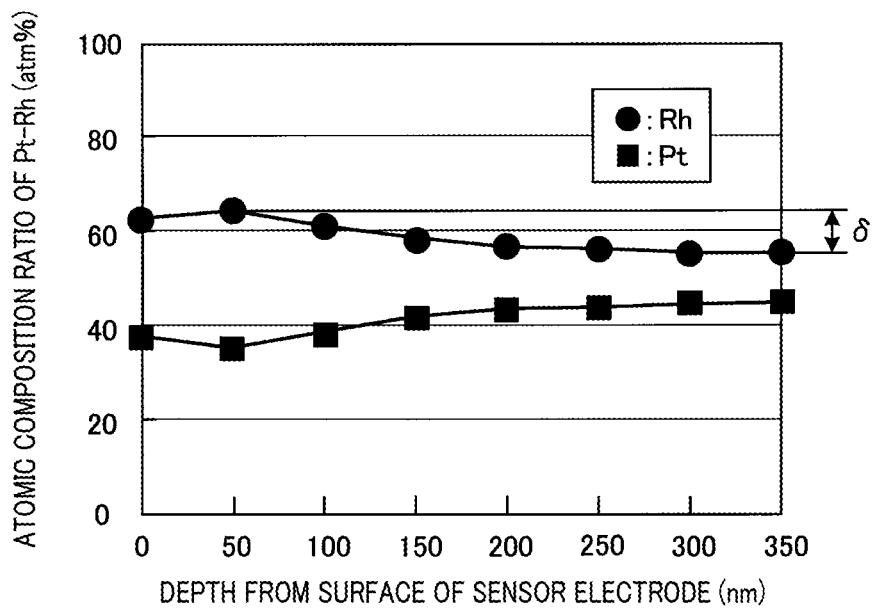
FIG. 17 is a graph which represents a relation between a depth (nm) from an outer surface of a sensor electrode and a distribution (atom %) of an atomic composition ratio of Pt to Rh in a surface layer of the sensor electrode according to an embodiment.

FIG. 17 represents a relation between the depth (nm) from the surface 220 of the sensor electrode 22 and the distribution of an atomic composition ratio between Pt and Rh (atom %) in the surface layer 221 of the sensor electrode 22. In this case, the atomic composition ratio of Pt to Rh contained in the Pt—Rh alloy in the whole of the sensor electrode 22 is Pt:Rh=45:55.

FIG. 17 shows that the percentage of Rh around the surface 220 of the sensor electrode 22 is high, and that as the depth from the surface 220 of the sensor electrode 22 is increased from 0 nm to 350 nm, the ratio of Pt to Rh in the surface layer 221 of the sensor electrode 22 approaches the ratio of Pt to Rh in the whole of the sensor electrode 22.

In FIG. 17, a difference δ between a maximum value and a minimum value of the percentage of Rh contained in the Pt—Rh alloy of the surface layer 221 of the sensor electrode 22 is less than or equal to 10 atom %. This eliminates an excessive difference between the percentage of Rh in the Pt—Rh alloy in the whole of the sensor electrode 22 and the percentage of Rh in the Pt—Rh alloy of the surface layer 221 of the sensor electrode 22.

When the difference S between the maximum value and the minimum value of the percentage of Rh contained in the Pt—Rh alloy of the surface layer 221 of the sensor electrode 22 is higher than 10 atom %, it may result in a risk that Rh concentrates around the surface 220 of the sensor electrode 22, so that Rh is diffused early when the NOx sensor 1 is in use.

Figure 18:
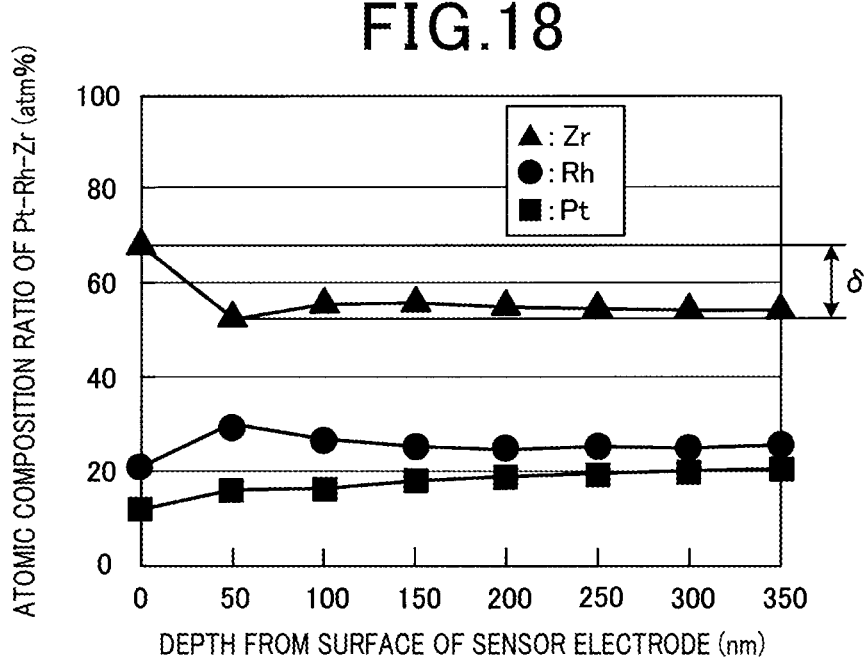
FIG. 18 is a graph which represents a relation between a depth (nm) from an outer surface of a sensor electrode and a distribution (atom %) of an atomic composition ratio among Pt, Rh, and Zr in a surface layer of the sensor electrode according to an embodiment.

FIG. 18 represents a relation between the depth (nm) from the surface 220 of the sensor electrode 22 and the distribution of an atomic composition ratio among Pt, Rh, and Zr (atom %) in the surface layer 221 of the sensor electrode 22.

In this case, the atomic composition ratio of Pt to Rh contained in the Pt—Rh alloy in the whole of the sensor electrode 22 is Pt:Rh=45:55. The atomic composition ratio of the Pt—Rh alloy to Zr in the whole of the sensor electrode 22 is Pt—Rh alloy:Zr=75:25.

FIG. 18 shows that a ratio of Zr to Rh is high around the surface 220 of the sensor electrode 22, that as the depth from the surface 220 of the sensor electrode 22 is increased from 0 nm to 350 nm, the ratio of Pt to Rh in the surface layer 221 of the sensor electrode 22 gradually approaches the ratio of Pt to Rh in the whole of the sensor electrode 22, and that the ratio of the Pt—Rh ally to Zr in the surface layer 221 of the sensor electrode 22 gradually approaches the ratio of the Pt—Rh alloy to $ZrO_2$ (Zr) in the whole of the sensor electrode 22.

The percentage of Zr in the surface layer 221 of the sensor electrode 22 is predominantly higher than that in the whole of the sensor electrode 22. The percentage of such a component in the whole of the sensor electrode 22, therefore, appears only when the depth from the surface 220 of the sensor electrode 22 is greater than about 1,000 nm or more. In FIG. 18, the percentage of the component in the whole of the sensor electrode 22 does not appear.

In FIG. 18, a difference δ between a maximum value and a minimum value of the percentage of Zr contained in the sum of the Pt—Rh alloy and Zr in the surface layer 221 of the sensor electrode 22 is less than or equal to 30 atom %. This eliminates an excessive difference between the percentage of $ZrO_2$ (Zr) in the whole of the sensor electrode 22 and the percentage of Zr in the surface layer 221 of the sensor electrode 22. When the difference S between the maximum value and the minimum value of the percentage of Zr in the surface layer 221 of the sensor electrode 22 is higher than 30 atom %, it may result in a risk that the percentage of Zr in the surface layer 221 of the sensor electrode 22 early approaches that in the whole of the sensor electrode 22.

Figure 19:
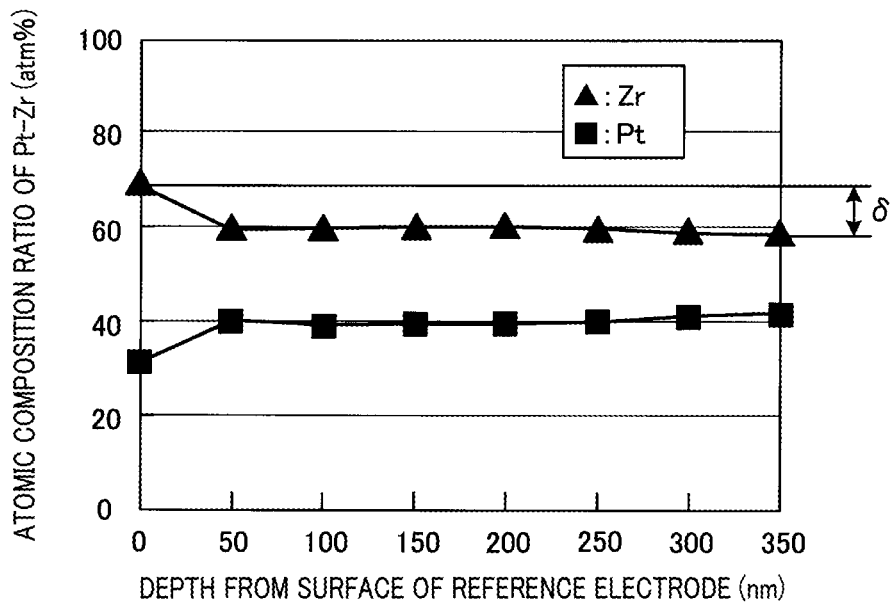
FIG. 19 is a graph which represents a relation between a depth (nm) from an outer surface of a reference electrode and a distribution (atom %) of an atomic composition ratio of Pt to Zr in a surface layer of the reference electrode according to an embodiment.

FIG. 19 represents a relation between the depth (nm) from the surface 240 of the reference electrode 24 and the distribution of an atomic composition ratio between Pt and Zr (atom %) in the surface layer 241 of the reference electrode 24. In this case, the atomic composition ratio of Pt to Zr in the whole of the reference electrode 24 is Pt:Zr=87.5:12.5.

FIG. 19 shows that the percentage of Zr is high around the surface 240 of the reference electrode 24, and that as the depth from the surface 240 of the reference electrode 24 is increased from 0 nm to 350 nm, the ratio of Pt to Zr in the surface layer 241 of the reference electrode 24 gradually approaches that in the whole of the reference electrode 24.

The percentage of Zr in the surface layer 241 of the reference electrode 24 is predominantly higher than that in the whole of the reference electrode 24. The percentage of such a component in the whole of the reference electrode 24 will, therefore, appear only when the depth from the surface 240 of the reference electrode 24 is greater than about 1,000 nm or more. In FIG. 19, the percentage of the component in the whole of the reference electrode 24 is not shown.

In FIG. 19, a difference δ between a maximum value and a minimum value of the percentage of Zr in the surface layer 241 of the reference electrode 24 is less than or equal to 25 atom %. This eliminates an excessive difference between the percentage of $ZrO_2$ (Zr) in the whole of the reference electrode 24 and the percentage of Zr in the surface layer 241 of the reference electrode 24.

When the difference S between the maximum value and the minimum value of the percentage of Zr in the surface layer 241 of the reference electrode 24 is higher than 25 atom %, it may result in a risk that the percentage of Zr in the surface layer 241 of the reference electrode 24 early approaches that in the whole of the reference electrode 24.

As apparent from the above discussion, in the NOx sensor 1 of this embodiment, the atomic composition ratio between Pt and Rh in the surface layer 221 of the sensor electrode 22 is defined. The atomic composition ratio between the Pt—Rh alloy and Zr in the surface layer 221 of the sensor electrode 22 is defined. Further, the atomic composition ratio between Pt and Zr in the surface layer 241 of the reference electrode 24 is defined. This minimizes the current change rate X in the sensor electrode 22 and also shortens the activation time T of the sensor electrode 22, thereby ensuring an enhanced ability of the NOx sensor 1 to decompose NOx over an increased period of time.

What is claimed is:

1. A NOx sensor comprising:
    one or a plurality of solid electrolyte bodies which have oxygen ion conductivity;
    a pump electrode which is disposed on a surface of the solid electrolyte body which is exposed to measurement gas containing oxygen, the pump electrode being used to regulate an oxygen concentration in said measurement gas; and
    a sensor electrode which is disposed on the surface of the solid electrolyte body which is exposed to the measurement gas and is used to measure a concentration of NOx in the measurement gas whose oxygen concentration has been regulated,
    wherein a metallic component of the sensor electrode is a Pt—Rh alloy,
    wherein a mass ratio of Pt to Rh in a whole of the sensor electrode is Pt:Rh=70:30 to 35:65, and
    wherein a percentage of Rh in the Pt—Rh alloy in a surface layer ranging from an outer surface of the sensor electrode to a depth of 350 nm is higher than a percentage of Rh in the Pt—Rh alloy in a whole of the sensor electrode by an atomic composition percentage of 4 to 10 atom %.

2. A NOx sensor as set forth in claim 1, wherein a difference between a maximum value and a minimum value of the percentage of Rh in the Pt—Rh alloy in the surface layer of the sensor electrode is less than or equal to 10 atom %.

3. A NOx sensor as set forth in claim 1, wherein the sensor electrode contains $ZrO_2$ in addition to the Pt—Rh alloy, wherein a mass ratio of the Pt—Rh alloy to Zr in a whole of the sensor electrode is Pt—Rh alloy: Zr=93:7 to 75:25, and wherein a percentage of Zr in a sum of the Pt—Rh alloy and Zr in the surface layer of the sensor electrode is higher than a percentage of Zr in sum of the Pt—Rh alloy and Zr in a whole of the sensor electrode by an atomic composition percentage of 25 to 55 atom %.

4. A NOx sensor as set forth in claim 3, wherein a difference between a maximum value and a minimum value of the percentage of Zr in the sum of the Pt—Rh alloy and Zr in the surface layer of the sensor electrode is less than or equal to 30 atom %.

5. A NOx sensor as set forth in claim 1, further comprising a reference electrode which is disposed on a surface of the solid electrolyte body which is exposed to a reference gas containing a constant concentration of oxygen, the reference electrode being opposed to the sensor electrode, and wherein the reference electrode contains Pt and $ZrO_2$, a mass ratio of Pt to Zr in a whole of the reference electrode being Pt:Zr=97:3 to 85:15, and wherein a percentage of Zr in sum of Pt and Zr in a surface layer of the reference electrode ranging from a surface of the reference electrode to a depth of 350 nm is higher than a percentage of Zr in sum of Pt and Zr in a whole of the reference electrode by an atomic composition percentage of 40 to 65 atom %.

6. A NOx sensor as set forth in claim 5, wherein a difference between a maximum value and a minimum value of the percentage of Zr in the sum of Pt and Zr in the surface layer of the reference electrode is less than or equal to 25 atom %.

7. A NOx sensor as set forth in claim 5, wherein the pump electrode and the sensor electrode are disposed on the surface of the single solid electrolyte body which is exposed to the measurement gas, and wherein the reference electrode is disposed on the surface of the single solid electrolyte body which is exposed to the reference gas.

\* \* \* \* \*

UNITED STATES PATENT AND TRADEMARK OFFICE
CERTIFICATE OF CORRECTION

| | | |
|---|---|---|
| PATENT NO. | : 10,288,580 B2 | Page 1 of 1 |
| APPLICATION NO. | : 15/542219 | |
| DATED | : May 14, 2019 | |
| INVENTOR(S) | : Nakatou et al. | |

It is certified that error appears in the above-identified patent and that said Letters Patent is hereby corrected as shown below:

On the Title Page

At Item (54) and at Column 1, Line 1 in the Specification, the title reads:
NOX SENSOR The title should be:
NOx SENSOR At Item (30) The Foreign Application Priority Data reads:
Nov. 27, 2015 (JP) ................... 2015-232151

The Foreign Application Priority Data should be:
Jan. 8, 2015 (JP) ..................... 2015-002387
Nov. 27, 2015 (JP) ................... 2015-232151

Signed and Sealed this
Sixteenth Day of July, 2019

Andrei Iancu
*Director of the United States Patent and Trademark Office*